United States Patent
Halsne et al.

(10) Patent No.: US 12,211,613 B2
(45) Date of Patent: *Jan. 28, 2025

(54) RAPID RESPONSE SYSTEM FOR CARDIAC ARREST

(71) Applicant: KONINKLIJKE PHILIPS N.V., Eindhoven (NL)

(72) Inventors: Eric Grant Halsne, Kenmore, WA (US); Bente De Lat, Utrecht (NL); Dawn Blilie Jorgenson, Mercer Island, WA (US); Dennis E. Ochs, Woodinville, WA (US); Jens Muehlsteff, Achen (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/138,321

(22) Filed: Apr. 24, 2023

(65) Prior Publication Data

US 2023/0335265 A1 Oct. 19, 2023

Related U.S. Application Data

(63) Continuation of application No. 16/496,470, filed as application No. PCT/EP2018/058337 on Mar. 30, 2018, now Pat. No. 11,657,910.

(60) Provisional application No. 62/478,718, filed on Mar. 30, 2017.

(51) Int. Cl.
*G16H 40/67* (2018.01)
*A61N 1/39* (2006.01)
*G08B 27/00* (2006.01)
*G16H 40/20* (2018.01)
*H04L 67/12* (2022.01)
*H04W 4/02* (2018.01)

(52) U.S. Cl.
CPC ........... *G16H 40/20* (2018.01); *A61N 1/3904* (2017.08); *G08B 27/001* (2013.01); *G16H 40/67* (2018.01); *H04L 67/12* (2013.01); *H04W 4/02* (2013.01)

(58) Field of Classification Search
CPC .... G08B 27/001; G08B 27/005; G16H 40/20; G16H 40/67; H04L 67/12
See application file for complete search history.

(56) References Cited

U.S. PATENT DOCUMENTS 8,559,913 B2 10/2013 Thijs
2005/0131740 A1 6/2005 Massenzio
(Continued)

OTHER PUBLICATIONS

International Search Report for PCT/EP2018/058337 filed Jul. 2, 2018.

*Primary Examiner* — Lynsey C Eiseman
*Assistant Examiner* — Skylar Lindsey Christianson

(57) ABSTRACT

An improved emergency response system includes a set of databases which relates to volunteer responders and patients, which is controlled by a central system computer. The system interacts with patients and volunteer responders through a wireless network to patient and volunteer communicator devices. The emergency response system calculates and provides a compensation to the volunteer responders based upon their on-duty time, proximity to enrolled patients, and optionally based upon their performance during training and cardiac rescue events.

18 Claims, 6 Drawing Sheets

(56) References Cited

U.S. PATENT DOCUMENTS

| | | | |
|---|---|---|---|
| 2007/0218869 A1* | 9/2007 | Thijs | G08B 25/016 |
| | | | 455/404.2 |
| 2009/0204434 A1 | 8/2009 | Breazeale | |
| 2014/0266718 A1 | 9/2014 | Bongberg | |
| 2016/0100302 A1 | 4/2016 | Barash | |
| 2017/0004427 A1 | 1/2017 | Bruchal | |
| 2017/0021185 A1* | 1/2017 | Das | H04W 4/023 |

* cited by examiner

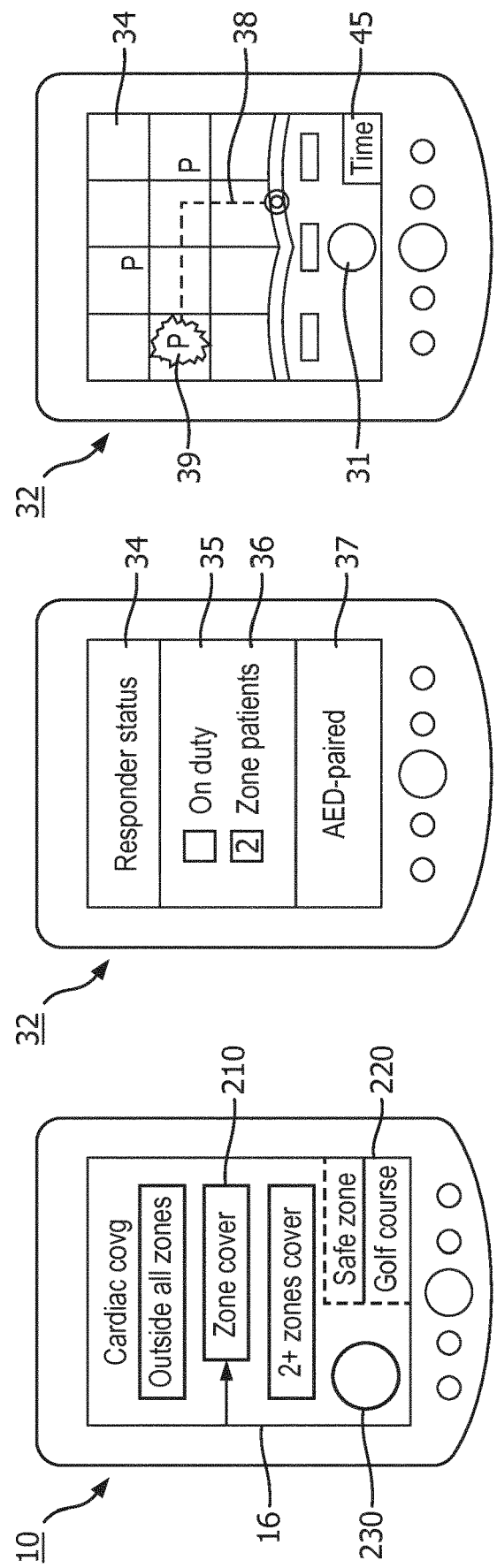

RAPID RESPONSE SYSTEM FOR CARDIAC ARREST

CROSS REFERENCE TO RELATED APPLICATIONS

This application is a Continuation application of U.S. patent application Ser. No. 16/496,470 filed on Sep. 23, 2019 and published in the English language on Nov. 26, 2020 as US 2020/0373005 A1, which is the U.S. National Phase application under 35 U.S.C. § 371 of International Application No. PCT/EP2018/058337, filed on Mar. 30, 2018 and published in the English language on Oct. 4, 2018 as WO 2018/178358 A1, which claims the benefit of U.S. Provisional Patent Application No. 62/478,718 filed on Mar. 30, 2017. These applications are hereby incorporated by reference herein.

The invention relates to an improved system and method for connecting a population of informal caregivers to a population of patients-at-risk, in particular those at risk for cardiac arrest. The system includes a communications network for responders and patients, as well as a method for compensating responders for participating in the system.

Sudden cardiac arrest (SCA) is a life-threatening medical condition in which the patient's heart fails to provide blood flow to support life. A defibrillator (AED) can be used to deliver defibrillating shocks to a patient suffering from cardiac arrest. But the chances of survival following a sudden cardiac arrest decrease about 10% for every minute of delay from onset to defibrillation treatment. Cardiac response must therefore be ideally provided within 6 minutes from the onset of cardiac arrest.

Traditional emergency response systems typically cannot respond quickly enough to out-of-hospital SCA, and therefore the involvement of bystanders or volunteers can improve response times. Several communities have deployed AEDs into public spaces, and have enlisted police, teachers, and the like to respond. Wireless communications such as smartphones and internet connections with incorporated locator systems may also leverage location knowledge to quickly bring responders to the patient's side. Cardiac related programs such as www.PulsePoint.org have also been launched that relay emergency requests to nearby care providers. Geographic Information Systems (GIS) may also be incorporated into the response system to intelligently deploy responders and AEDs to those locales most likely to experience a SCA.

Co-assigned U.S. Pat. No. 8,559,913B2, entitled "Emergency response device for summoning a responder and routing said responder to a victim" and herein incorporated by reference, is one example of a prior art cardiac response system. This reference relates to a system which detects the location of a cardiac emergency, and then which activates emergency response equipment and notifies personnel that are nearby.

Similarly, US2005131740A1, entitled "Management tool for health care provider services", relates to a system that provides health care service to the patient during emergency and monitors service providing caregiver at remote locations. The system automatically assigns geographically proximate caregiver to the patient during emergency and includes a payment processing module that determines an appropriate billing amount for the caregiver based on time spent at the patient location and the service provided by him. The system also includes a field device (cellular telephone) for both the patient and the caregiver that shows location of the patient to the caregiver and caregiver information to the patient respectively.

US2016100302A1, entitled "Community-Based Response System", relates to a system that automatically provides immediate responses during emergency situations (cardiac attack). The system identifies and assigns a lay responders who are proximal to the patient having a medical problem and also includes a notification system that tracks the performance of lay responders and rate/rank them as adept responders based on how many times the responders are notified & how often they responded to the notifications. The system also provides token of appreciation to the responder.

US2009204434A1, entitled "Healthcare Tracking", relates to a computer-implemented method that automatically computes a bill amount for the caregiver based on the location-time data generated automatically by the caregiver's mobile device and the number of the patients that the caregiver handles, wherein the location-time data of the healthcare provider is correlated with the location of a patient to determine an amount of time the caregiver spent at the patient location. The system uses pay-for-performance type program that tracks the time that the physician requires to perform a procedure & the number of complications associated with the procedure and attempts to award the physicians who performs the procedure quickly or efficiently with high quality. The method also provides a report to the patient which indicates the amount of care they have received to better understand what they have received for their money.

Each of the prior art references suffer from the problem of failing to optimize voluntary response to cardiac arrest emergencies when they occur outside of the hospital. Although the annual number of out-of-hospital SCA is high, the rate of occurrence in a particular locale is typically very low. Trained community responders often are not positioned to respond to an SCA event for months or even years. The relatively low frequency of occurrence can cause the erosion of participation and effectiveness of community volunteer response programs. In addition, a potential patient population may not be willing to pay for the service, as it is not clear what level of support they would get. Many volunteer care providers would also find it difficult to purchase an AED for the sole purpose of helping others, especially if the provider receives no compensation for participation. Finally, the currently available response system programs may not be fully trustworthy, because it is not clear if there will be a caregiver in the vicinity of an SCA that may actually respond.

Thus what is needed is a system and method for enhancing the participation and effectiveness of a voluntary community response system for SCA. Such an improved system must avoid or minimize the problems presented by the prior art.

In accordance with the principles of the present invention, a system and method for administering a community SCA response system is described, one which coordinates the participation of potential patients and responders in a particular geographic area. The invention includes wireless communicators which are carried by caregivers and optionally patients-at-risk of SCA, the communicators networked together through a communications network to a central provider. A computer at the central provider manages the volunteer participation, provides indications amongst all participants of SCA coverage, and calculates an incentive to volunteers as a function of their participation, e.g. an on-duty time and/or response to emergencies. The invention provides an indication (e.g. a dashboard) to both caregivers and patients-at-risk showing the coverage provided by the system by uniquely linking nearby caregivers to patients-at-risk. Accordingly, a financial compensation may be automatically established based on the coverage provided such that patients-at-risk only pay for the coverage they received. Care providers are compensated in accordance with the number of patients-at-risk they care for. Optionally, the compensation cost of the service to patient subscribers is made dependent on the quality-of-service, e.g. the availability coverage by nearby caregivers.

An improved cardiac emergency response system is described which comprises a patient wireless communicator having a display of a patient dashboard, the patient wireless communicator configured to display a representation of the patient wireless communicator location relative to a zone of cardiac coverage. The system also includes a responder wireless communicator having a display of a responder dashboard, the responder wireless communicator configured to display a representation of the responder wireless communicator location relative to the patient wireless communicator. A central station in wireless communication with the patient wireless communicator and the responder wireless communicator is configured to receive a cardiac emergency response notification and to responsively transmit a cardiac response request to the responder wireless communicator, the central station including a patient database with a set of patient identifying data and a responder database with a set of responder identifying data. The central station includes a computer which executes software instructions for determining the zone of cardiac coverage as a function of the responder wireless communicator location, a location of the patient wireless communicator relative to the zone of cardiac coverage, and a compensation to a responder in the responder database based on the zone of cardiac coverage, a pre-determined on-duty time, and the patient wireless communicator location.

In other embodiments, the system includes an automated external defibrillator (AED) having an AED communicator configured to communicate with one of the central station and the responder wireless communicator, wherein the central station further determines a location of the AED relative to the responder wireless communicator. The compensation is further based on the AED location. Compensation may be monetary, or may be a subscription as a patient participant.

In other embodiments, the compensation to the provider may be based upon a response time of the responder to a cardiac response request, to a proficiency level of cardiac rescue training, or to the number of patients covered in a given period of time. If provider participation is not effective, the system may disenroll that provider.

In other embodiments, the system assesses the participation of patients by determining a false alert rating. The system may adjust the patient subscription or participation if the rating is poor.

In accordance with other principles of the invention, a method for administering a cardiac emergency response system comprises the steps of providing the aforementioned cardiac emergency response system, determining the zone of cardiac coverage as a function of the responder wireless communicator location, determining a location of the patient wireless communicator relative to the zone of cardiac coverage, displaying a zone of cardiac coverage on the patient wireless communicator display, and displaying a patient location on the responder wireless communicator display. Optional steps in the method may be enrolling a responder associated with the responder wireless communicator in the responder database, compensating the responder based on an overlap of the zone of cardiac coverage with the patient location, or of automatically generating recommendations to increase an overlap of the zone of cardiac coverage with the patient location. Optionally, a step of displaying a predetermined AED safe zone having a fixed location on the patient wireless communicator display is provided.

In accordance with other principles of the invention, a non-transitory storage medium for a computer, readable and executable for executing instructions by an electronic processor is described for implementing the steps of the aforementioned method.

IN THE DRAWINGS

FIG. 2 illustrates an embodiment of a patient wireless communicator and dashboard display.

FIG. 3a illustrates one embodiment of a responder wireless communicator and dashboard display. FIG. 3b illustrates another embodiment of a responder wireless communicator and dashboard display.

DETAILED DESCRIPTION OF THE PREFERRED EMBODIMENTS

Figure 1:
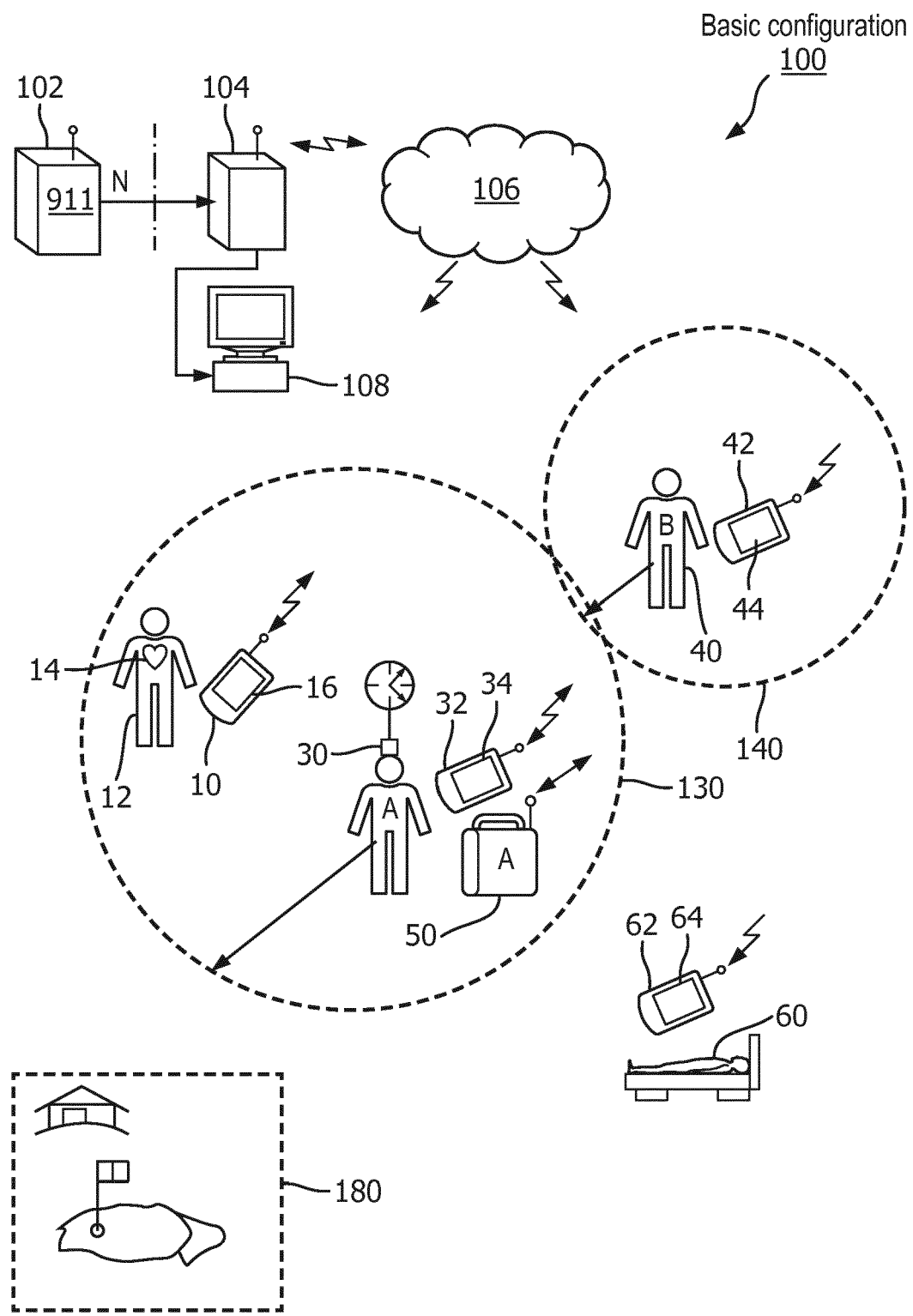
FIG. 1 illustrates a basic configuration diagram of the overall improved cardiac emergency response system.

In a preferred embodiment of the system, awareness of the care environment is two-way. Patients-at-risk have continuous visibility of the care providers around them, including an indication of which care providers are currently assigned to help them in case of a cardiac arrest. Care providers will have a similar dashboard which displays the patients-at-risk for which they are responsible at any given time.

A request for help is optionally triggered by a sensor that is worn by the patient-at-risk. When the sensor detects a sudden cardiac arrest, the patient will get a warning. If she does not then 'mute' the alarm, a nearby care provider will be automatically notified for help. Exemplary sensors may be integrated into a (smart) watch, or may be in the form of a patch that measures ECG signals.

In yet another embodiment of the inventive method, patients are guided in finding "AED safe" places or zones. For example, restaurants, golf courses and the like which might have AEDs and/or trained responders on staff may be displayed on the patient communicator. Alternatively, AED safe zones might be those in which a targeted and on-duty responder is currently nearby. The guidance could be provided by means of software instructions in the form of a smartphone application.

In a further embodiment, both care providers and patients-at-risk receive a 'karma rating' depending on their compliance. For example, patients that trigger excessive false alarms may be rated lower. Care providers that are consistently responsive at a high level may be rated higher. Patients-at-risk that trigger many false alarms may see their service fee go up compared to patients that do not trigger false alarms. Similarly, care givers that always respond (and quickly) may be compensated at a higher rate than the ones that don't.

In a further embodiment, an incentive for the care provider is based on the value they can add to a cardiac rescue. Such value may be based on factors such as whether or not they 1) carry an AED or are only able to do CPR; 2) have had their (regular) CPR training; 3) are most of the time close to many patients-at-risk with no or little other caregivers around; 4) have a track record of always showing on the scene; and/or 5) have a low average response time.

To further optimize the system and improve response time, each targeted responder's dashboard may display the location of a high risk patient's home ahead of time. This has the advantage of faster arrival time for the responder because they are familiar with the location and also may have higher confidence they have arrived at the correct home. Additional enhancements could include the ability to automatically unlock the door to home of the patient.

The method described in the embodiments can also be used without a dashboard. For example, a dashboard may not be necessary at all if it is preferred to implement the method in a current first responder system, but would preferably incorporate the inventive compensation system. In such a system, the algorithm for adjusting compensation would be used, such as the below-described 'coverage-algorithm/data-analysis' of available care givers and current care takers. The coverage-algorithm may be used to:

give specific/'personalized' support and advise to municipalities in order to improve the coverage rate in certain (low-coverage) areas;
directly show the coverage rate to care givers, care takers or third parties/emergency organizations;
generate insights in how many people can potentially be rescued with an optimum numbers of care givers;
determine the amount of compensation for care givers; and/or
determine the amount of service fee (value-based service fee) for care takers.

Now turning to the illustrations, FIG. 1 illustrates a basic configuration of an overall improved cardiac emergency response system 100, according to the invention. System 100 comprises three parts: one or more responder wireless communicators; one or more patient wireless communicators, and; a centralized management system to administer the system.

A responder wireless communicator is intended to be co-located with each responder in the system. Shown in FIG. 1 is a responder wireless communicator 32 for a responder who is nearby a patient 12, a second responder wireless communicator 42 with a second responder 40 who is on-duty but not nearby patient 12, and an off-duty responder 60 with a third responder wireless communicator 62. Each wireless communicator may be in the form of a commercial smartphone running a customized software application, or may be a custom hardware device. Each communicator 32/42/62 preferably includes a dashboard display 34/44/64. As will be shown in FIG. 3, each dashboard display indicates current duty status of the co-located responder and of the system.

A patient wireless communicator 10 is intended to be co-located with each patient 12 subscribing to the system. The patient wireless communicator 10 may be in the form of a commercial smartphone running a customized software application, or may be a custom hardware device. The communicator 10 preferably includes a patient dashboard display 16. As will be shown in FIG. 2, the patient dashboard display 16 indicates the level of cardiac zone coverage at the patient's current location and may indicate the current location of nearby cardiac zones. Patient communicator 10 may also have a call acknowledgement or alarm button 31 for initiating a response.

Patient 12 may optionally be coupled to a patient cardiac monitor 14, which may be a cardiac "patch" or a handheld device which continuously monitors the patient's cardiac health. Such a monitor 14 preferably is in continuous wired or wireless communication with the patient wireless communicator 10, so that a detected cardiac emergency may be immediately conveyed to the system 100. One example of a "patch" patient cardiac monitor 14 is described in co-assigned U.S. Pat. No. 9,510,755 entitled "ECG monitoring system with docking station", which is hereby incorporated by reference.

A central station 104 manages the interaction between the responder communicator(s) and the patient communicator. Central station 104 is preferably in wireless communication with all system communicators via a standard wireless communication network 106. Control of central station 104 is provided by a computer 108 which executes software instructions for managing the system 100, such as for determining zones of cardiac coverage, locations of patients relative to the zones, and for compensating responders accordingly. Computer 108 includes a non-transitory storage medium for a computer, readable and executable for executing instructions by an electronic processor for these functions. Preferably, central station 104 includes an interface with the locality emergency response (e.g. 911) system 102, such that alerts received at the 911 system are automatically provided via a communication link N as well.

On-duty responder 30 (shown with a clock representation over her head) preferably is co-located with a portable automated external defibrillator (AED) 50. AED 50 considerably enhances the treatment of a sudden cardiac arrest patient by being small enough and light enough to be carried to a patient's side quickly enough to apply an effective therapeutic defibrillating shock. AED 50 is preferably in communication with the responder communicator 32 such that central station 104 can maintain a record of the periods in which responder 30 is accompanied by the AED. As will be discussed in more detail, a compensation of the responder 30 may be based on the AED 50 presence.

FIG. 1 also illustrates the various zones in which interaction between patients and responders may or may not occur. A zone of cardiac coverage (ZCC) 130, for example, is created when a responder such as responder 30 enters an on-duty status. ZCC 130 is thereafter linked to the responder 30 geographic location, and moves with the responder. ZCC 130 represents the geographic area in which responder 30 is expected to respond immediately to a cardiac emergency. Although shown as a circle, ZCC may be of any appropriate shape that corresponds to a region which the responder 30 can reasonably access, such as within a building. Thus, if patient 12 experiences a cardiac emergency within ZCC 130, patient communicator 10 notifies the responder communicator 32 via central station 104.

FIG. 1 also shows a second responder 40 who is on duty and is thus within a second ZCC 140. Second ZCC 140 moves with the second responder 40 location, and represents the area in which the second responder will respond to a cardiac emergency. In this case, patient 12 is located outside of second ZCC 140. If patient 12 experiences and reports a cardiac emergency, the second responder wireless communicator 42 will not be activated. Similarly, off-duty responder 60 will not receive a response notification via third responder wireless communicator 62 because of her off-duty status.

FIG. 1 also illustrates a fixed-location AED safe zone 180. AED safe zone 180 may be locales which have AEDs and CPR-trained personnel that can quickly respond to a cardiac emergency. Examples of such AED safe zones 180 may be golf courses, fitness facilities, health care facilities, schools, fire and police stations, and the like. Information about AED safe zone 180 locations may be maintained at central station 104, or may be directly stored and displayed on the patient wireless communicator 10.

FIG. 2 illustrates an example patient wireless communicator 10 with a patient dashboard display 16. Display 16 is configured to provide the patient 12 information regarding her location relative to ZCC 130 and/or AED safe zone 180. Dashboard display of ZCC is shown by the boxes at 210, which may be highlighted to indicate the corresponding location, e.g. "outside all zones", "coverage by one zone", "coverage by multiple zones" and the like. Patient 12 may not need additional detail, such as the identity of the responder, in order to maintain appropriate anonymity and security in the system. In addition, dashboard display 16 may indicate where the patient is relative to a nearest AED safe zone at display 220. The identity of the AED safe zone, e.g. "golf course", may be provided there. A help call button 230 may be provided, either on the communicator 10 touch screen or on a designated hard button on the device.

FIG. 3a similarly illustrates an example responder wireless communicator 32 with a responder dashboard display 34. Dashboard display 34 includes a duty status display 35, which by for example a shaded or highlighted box shows the responder 30 whether or not they are on duty at that time. Dashboard display 34 also indicates whether and how many patients 12 are located within its current ZCC 130. This responder location indicator relative to patients 36 may be disposed as a highlighted box with the number of covered patients displayed within. Finally, dashboard display 34 may include an indication of AED pairing 37, which shows the responder that AED 50 is nearby, e.g. in the car trunk, in a carry bag, or in the same room.

FIG. 3b illustrates the responder dashboard display 34 which may be triggered on the responder wireless communicator 32 when an emergency cardiac response has been issued by central station 104. Responder dashboard display 34 may indicate a map showing the patient-in-distress location 39 and/or a response path 38 showing the fastest route from responder to patient location. The location of other patients P within the responder's ZCC may also be indicated. Preferably, responder wireless communicator 32 is configured to include a call acknowledgement button which, when pressed, notifies central station 104 that the responder 30 has received the emergency notification and has begun to respond. Display 34 may also include an elapsed time clock 45 to indicate the elapsed time since the emergency notification was received and/or alternatively since the device sensed the press of the call acknowledgment button 31.

Figure 4:
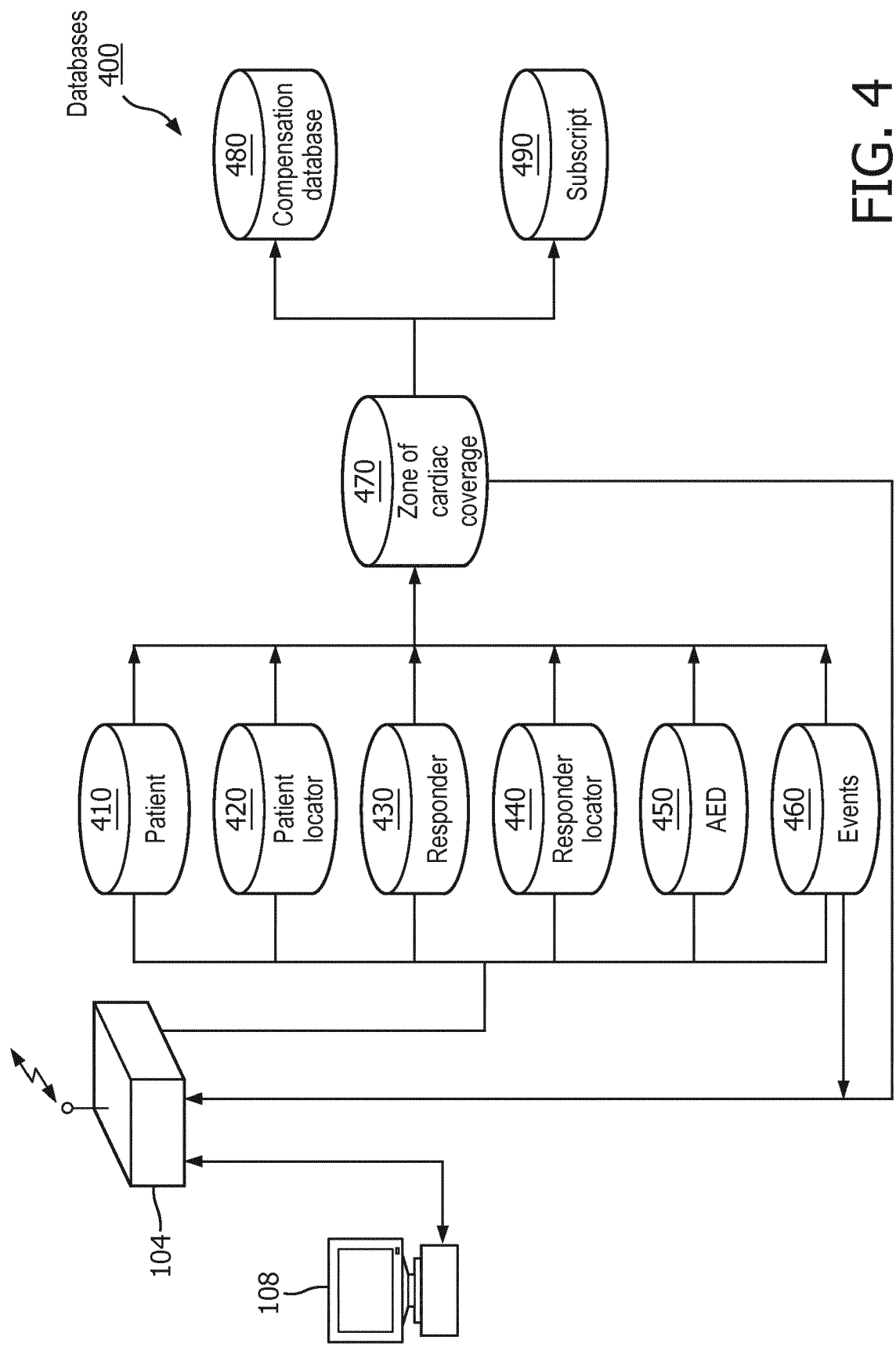
FIG. 4 illustrates one embodiment of a central station computer database system.

FIG. 4 illustrates an exemplary computerized information management arrangement for an emergency cardiac response system. The arrangement comprises the central station 104 which incorporates computer hardware, communications hardware, and software for controlling information flow between a set of databases 400. A computer 108 which is customized with software instructions for controlling central station 104 includes input and output devices so that an administrator can adjust the system operation. Alternative arrangements of the computerized components fall within the scope of the invention. For example, one or more of the databases 400 may be stand-alone devices, cloud-based devices, or may be included within computer 108 or central station 104. Communications interfaces may be included within computer 108 in addition to central station 104.

Databases 400 are collections of data, stored in computer hardware memory, which are logically grouped according to source and type. The groups are relationally connected as is known in the relational database modelling art. FIG. 4 illustrates various groupings of data, and their use in developing an efficient cardiac rescue scheme with zones of cardiac coverage. Also illustrated is the novel compensation scheme which is based upon the ZCC responses.

Each of the following described databases is in communication with central station 104, which is in turn configured to receive a cardiac emergency response notification and to responsively transmit a cardiac response request to a responder wireless communicator. Two databases needed for this functionality are a patent database 410 and a responder database 430. Patient database 410 includes patient identifying data such as name, address, health condition, wireless communicator 10 identifying formation, next of kin and other medical related data. Responder database 430 includes responder wireless communicator 32 identifying information, name, address, records of cardiac rescue training, duty status (on-duty or off-duty times), scheduling, and other rescue related data.

Two additional databases needed for system functionality are the patient locator database 420 and the responder locator database 440. These databases are continually updated with geo-location information for each patient in the system and for each responder in the system respectively. Optionally, information as to the type of location may be included, such as if the responder/patient location is in a vehicle, at work in an office building, or on foot. Fixed-location AED safe zone locations may also be provided in the responder locator database 440.

An AED database 450 may include ownership and use data for each AED 50 in the system 100. Use data may include the proportion of time that each AED 50 is in proximity to a respective responder wireless communicator 32, which in turn indicates how effective the responder may be to the system AED database 450 may also include use and maintenance data, so that the system 100 can automatically generate service calls and requests if, for example, the AED 50 battery is nearing the end of life AED database 450 preferably includes dynamic information indicating whether the AED is in service and with an on-duty responder.

An events database 460 may include responder past activity data, such as the responder's history of instances of response/non-response to alerts, time to acknowledge an alert, elapsed time of arrival to a patient location, and other information indicating the level and quality of participation by the responder in the system. Events database 460 may also include patient participation information such as the number of false alerts generated at the patient wireless communicator 10. A false alert rating for each patient may be generated from the false alert data.

Computer 108 executes software instructions using at least the responder database 430 and the responder locator database 440 to populate a zone of cardiac coverage database (ZCC database) 470. The ZCC database 470 is continuously updated to reflect each responder ZCC in the system. The shape, size, and location of each responder ZCC is determined as a function of the responder wireless communicator information in locator database 440. If the responder database 430 indicates that the responder is off duty, then there is no ZCC associated with that responder.

Computer 108 also executes software instructions using at least the patient locator database 420 to geo-locate each patient wireless communicator relative to each zone of cardiac coverage. Computer 108 continuously updates the patient location in the ZCC database 470 as well. Thus, the overlap between each patient location and each responder ZCC is maintained in the database.

A particular feature of system 100 is an inventive compensation feature for responders, which is based upon the determined zones of cardiac coverage, on-duty time, and relative location of patient wireless communicators to the ZCCs. Computer 108 executes software instructions to maintain a compensation database 480 for this purpose. Compensation database 480 is preferably continuously (or routinely) updated based upon the information collected in the ZCC database 470, as adjusted by compensation schemes that will be described in further detail. Compensation database 480 thus accumulates a record of a compensatory benefit for each responder in the system, based upon the responder's overall participation level and quality of responses in the system 100.

Compensation in database 480 may be monetary. Payment to the responder may optionally be made automatically by computer 108 through standard electronic payments methods. Compensation in database 480 may alternatively be in the form of a complimentary patient subscription for a person designated by the responder.

A subscription database 490 may track a patient participation in system 100. Each patient may be assessed a system subscription fee based upon the patient's level and quality of participation. For example, the fee may be based upon a determined patient false alert rating in order to compensate responders for excessive activity in responding to false alerts generated by the patient wireless communicator. Such adjustable fee structures are intended to improve overall efficiency of the system 100 by incenting patient subscribers to use the system properly.

Figure 5:
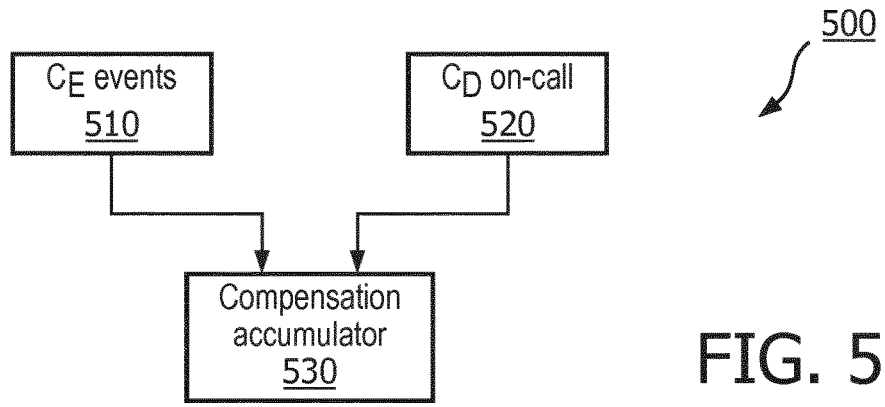
FIG. 5 illustrates a schematic embodiment of a responder compensation calculator.

FIG. 5 is a schematic illustration of a responder compensation calculator 500 which is executed by software instructions at computer 108, and results of which are preferably stored in compensation database 480. A compensation accumulator 530 collects data pertaining to a compensatory benefit for the responder in at least two ways. First, an events compensation calculator 510 determines a compensation benefit based upon the responder's actual participation in cardiac emergency events. Factors which may influence the events calculation are response time, whether or not an AED accompanies the responder wireless communicator, and other quality factors related to the actual event. Compensation accumulator 530 also collects data related to the responder's on-call or on-duty activity at on-call compensation calculator 520.

One exemplary method for determining compensation for on-call activity in calculator 520 is described with reference to FIG. 6. Patient locator database 420 and responder locator database 440 provide input data to the ZCC database 470 in order to determine overlap between each patient location (via the patient wireless communicators 10) and each determined ZCC 130. The responder locator database 440 also provides AED location information to the AED database 450 regarding AEDs 50 in the system as accompanying responders or located in AED safe zones 180. Responder database 430 provides input data to the on-call compensation calculator 520 portion pertaining to the duty status flag 630 and to a dynamic on-call periodic rate calculator portion 620 pertaining to a stored base compensation rate ratebase, Quality-of-care rate Qr, and Response rate Radj.

Figure 6:
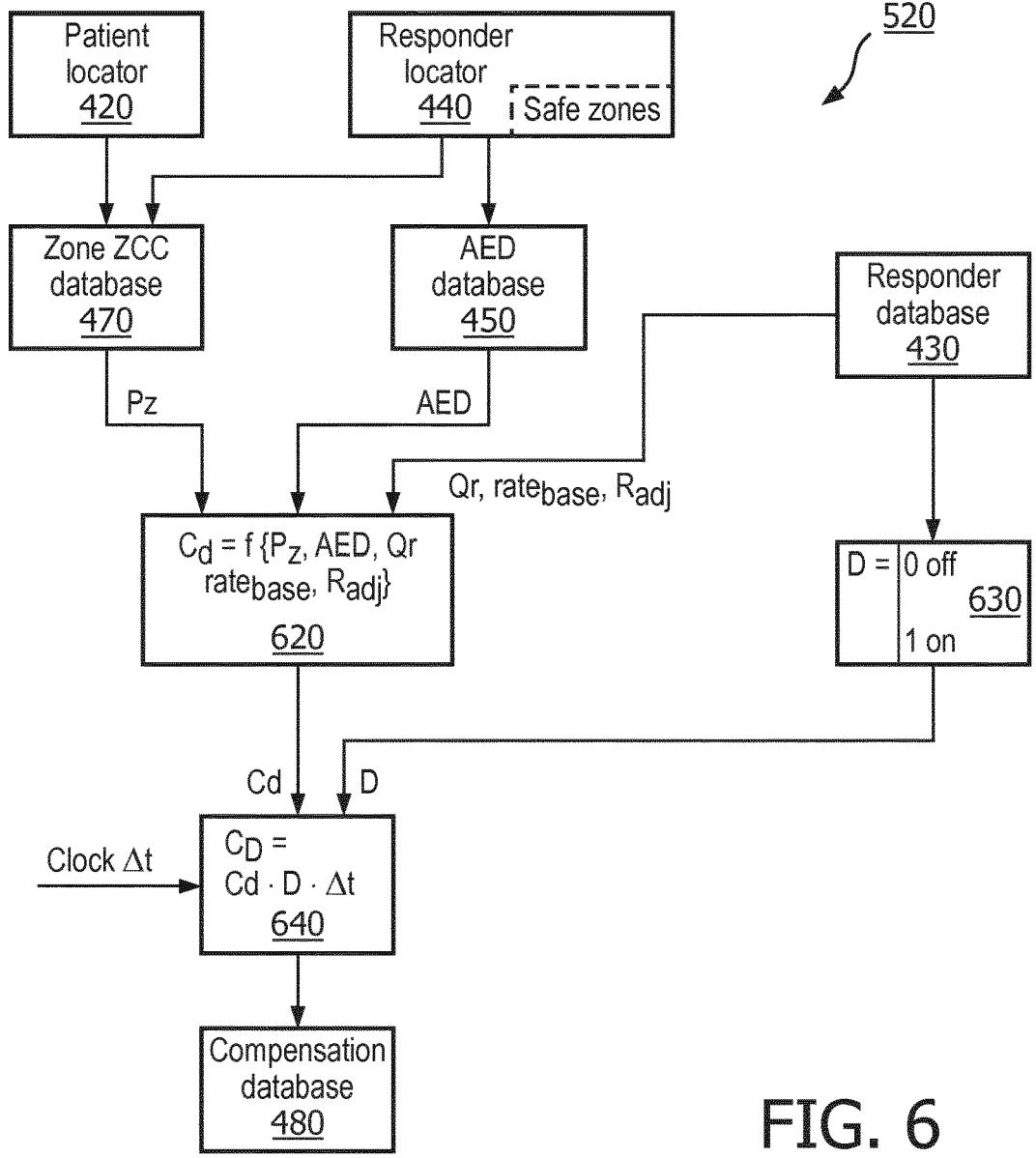
FIG. 6 illustrates a schematic embodiment of a responder on-call compensation calculator.

An exemplary determination of an adjusted on-duty rate at dynamic on-call periodic rate calculator portion 620 is also shown in FIG. 6. The adjusted on-duty rate Cd may be a function of the number of patients located within the responder ZCC Pz (as obtained from ZCC database 470), whether or not an AED 50 is currently associated with the responder wireless communicator from AED database 450, the quality-of-care rate Qr that may be based upon currency and level of training, a historical response rate Radj based upon whether and how fast the responder has responded to alerts in the past. A base compensation rate ratebase may apply equally to all participating responders in order to ensure that some minimal base amount may accumulate for the responder at a second, lower, level even if all patient wireless communicator locations lie outside of the zone of cardiac coverage.

One example of an equation for the adjusted on-duty rate might be $$Cd = Pz \times ratebase \times Qr \times Radj \times \{AED: 1 \text{ for AED associated}, 0.5 \text{ for no AED associated}\} \quad \text{Eq.1.}$$

The Cd output from calculator 620 and duty status flag 630 is provided to a periodic compensation calculator 640. Calculator 640 determines an accumulation amount for each marginal period of time {delta}t based on the responder duty status and the adjusted on-duty rate. A clock may provide each {delta}t.

No accumulation amount accrues if the responder is off-duty (D=0). As can be seen, the marginal accumulation amount CD can be calculated as $$CD = Cd \times D \times \{delta\}t \quad \text{Eq. 2.}$$

The marginal accumulation amount CD is then provided to compensation database 480 for further provision as a benefit to the responder.

Figure 7:
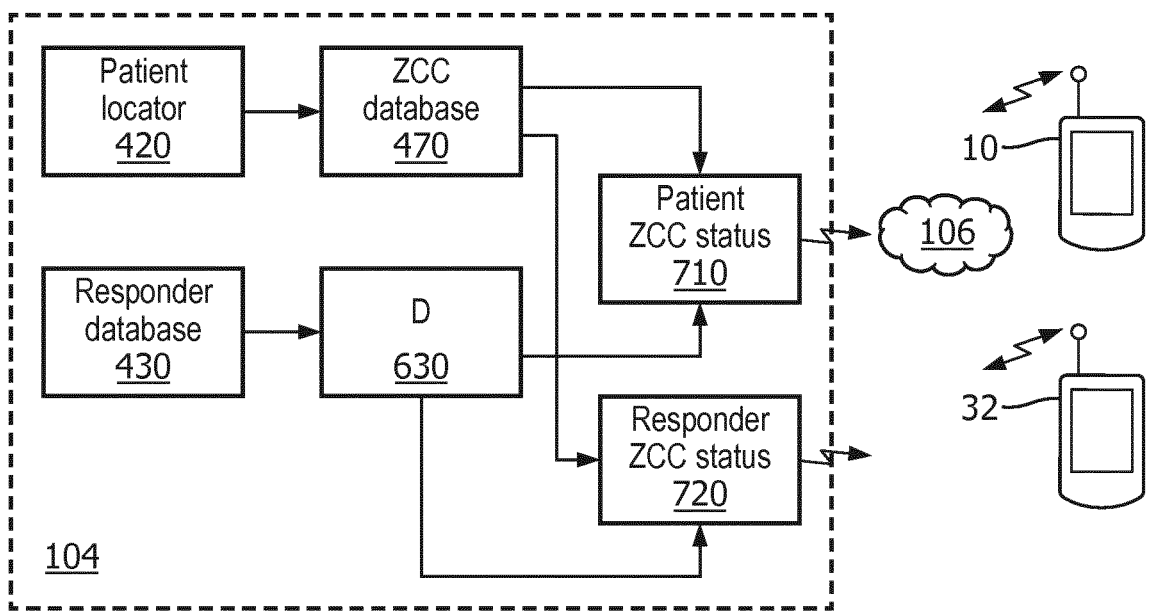
FIG. 7 illustrates an embodiment of a communications system connecting a patient and a responder.

FIG. 7 illustrates an embodiment of a communications system including central station 104. Central station 104 functions to connect a patient and a responder via a wireless communication network 106. As previously indicated, the patient 12 interacts with system 100 with wireless patient communicator 10, and the responder 30 interacts with system 100 with wireless responder communicator 32. Outputs from central station 104 of duty status from duty status flag 630 and relative patient/responder location from ZCC database 470 are provided to patient-ZCC overlap status output 710 and to a comprehensive responder ZCC status output 720. Output 710 is primarily provided to the patient wireless communicator 10 via network 106 to provide an indication to the patient as to whether or not they are covered by a ZCC or an AED safe zone. Output 720 is primarily provided to the responder wireless communicator 32 to provide an indication to the responder as to their duty status and how many patients are currently within their ZCC. Outputs 710 and 720 are previously described with reference to FIGS. 2 and 3.

Figure 8A:
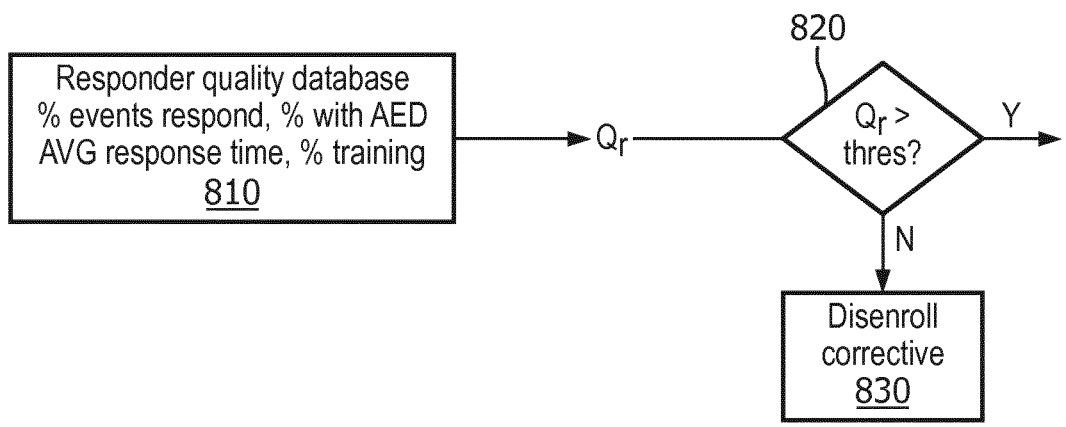
FIG. 8a illustrates a flowchart method for administering responder performance quality.

FIG. 8a illustrates a flowchart method for administering responder performance quality. As previously described, responder performance quality Qr may be used as a factor in calculating the responder compensation rate Cd and compensation CD. Responder database 430 preferably maintains quality-related data about each responder in a database portion labelled as a responder quality database 810. Quality database 810 in turn maintains data such as a proportion of alert events responded to, a proportion of event responses with an associated AED, an average event response time, and a current level of training completed. One or more of these factors may be used to calculate performance quality Qr.

Beyond use for compensation, FIG. 8a includes an additional feature at a responder quality threshold check step 820. If Qr for a particular responder fails to exceed a minimum predetermined quality threshold level at step 820, the responder is placed into a disenroll/corrective action status 830. For example, if the responder continually fails to obtain needed training, or fails to keep an AED at hand, corrective action may be initiated in order to improve the responder's performance quality. If corrective action subsequently fails, then the responder may be disenrolled from the system 100.

Figure 8B:
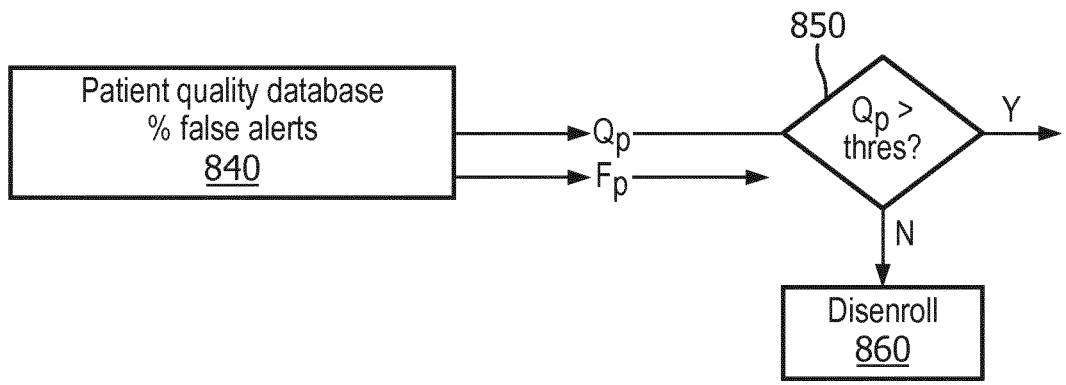
FIG. 8b illustrates a flowchart method for administering a patient activity quality.

FIG. 8b illustrates a flowchart method for administering a patient activity quality. As previously indicated, patient performance quality Qp may be used as a factor in calculating a subscription price Fp to a patient. Patient quality Qp may be determined for example based upon a proportion of false alert event initiations which have no reasonable basis in equipment malfunction or health indications. Data pertaining to patient quality is preferably maintained in the patient database 410, a subset of which is a patient quality database 840.

If Qp for a particular patient fails to exceed a minimum predetermined quality threshold level at step 850, the patient may be placed into a disenroll status at 860. For example, if the patient repeatedly activates the system 100 via wireless communicator 10 without reason, and corrective counseling fails to rectify the situation, then the patient may be disenrolled from the system 100.

Figure 9:
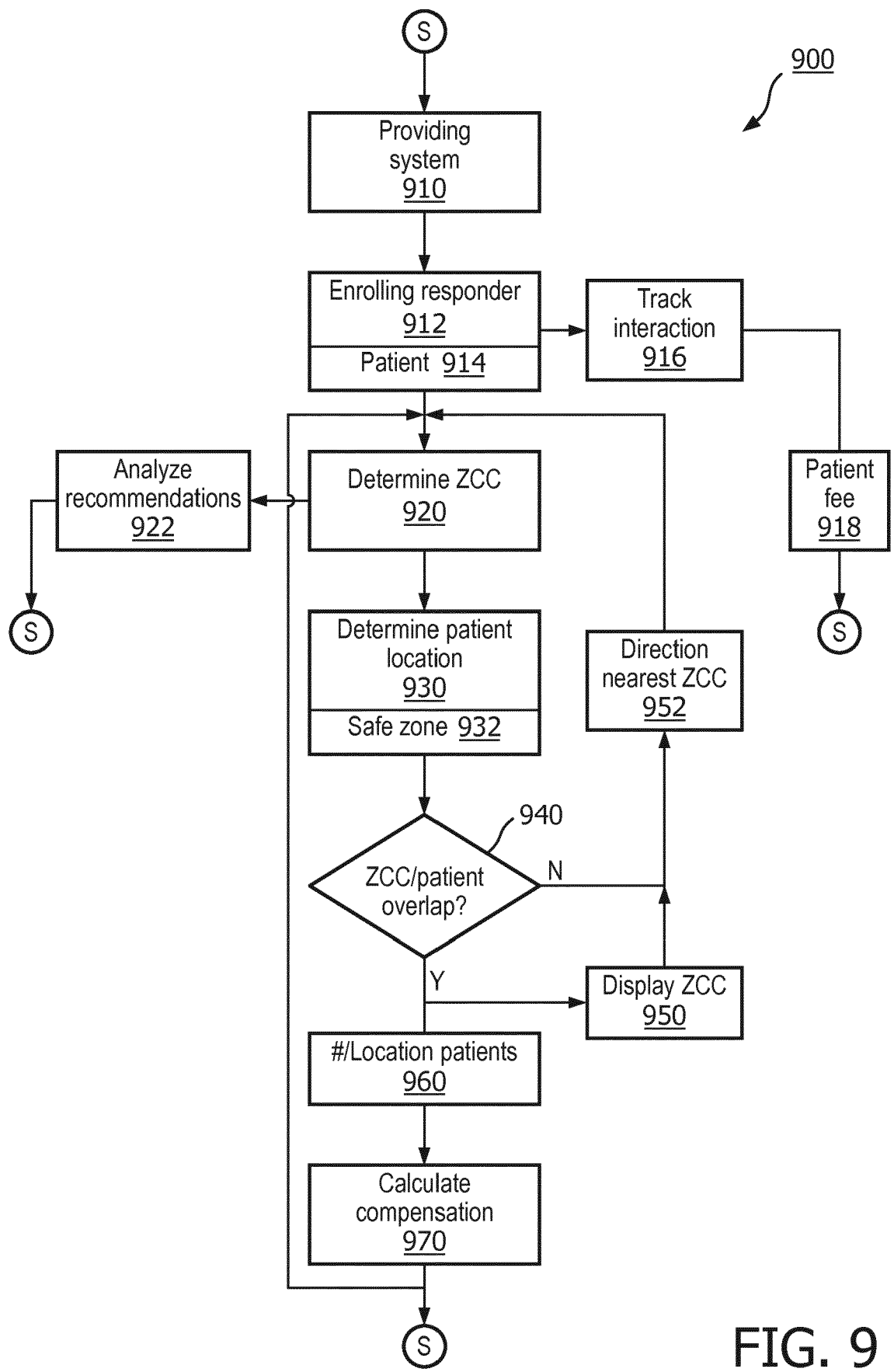
FIG. 9 illustrates a flowchart method for administering a cardiac emergency response system.

FIG. 9 illustrates a flowchart method 900 for administering a cardiac emergency response system. The method begins with a step of providing the cardiac emergency response system 910 similar to that described in reference to FIGS. 1 through 8. The provided system includes a patient wireless communicator with a patient dashboard display, a responder wireless communicator with a responder dashboard, and a central station in communication with both communicators. The system is configured to receive a cardiac emergency response notification and to responsively transmit a request to the responder communicator. One or more databases which include sets of patient identifying data and responder identifying data are also provided in this step 910.

Steps of enrolling the responder 912 and enrolling the patient 914 optionally follow the providing step. Enrolling steps 912 and 914 comprise associating responders with a responder wireless communicator and patients with a patient wireless communicator, and further comprise storing those associations in a responder database and patient database respectively.

With regards to the patient, step 916 comprises tracking patient interactions with system 100. Based upon the quality, quantity, and nature of the tracked interactions, a patient subscription fee for participating in the system 100 is determined at patient fee step 918. Not shown is a quality assessment step for each patient, which if not met, may optionally generate a subsequent disenrollment of patient from system.

A zone of cardiac coverage (ZCC) pertaining to each responder wireless communicator location is determined at step 920. As previously described, the zone is based upon the responder's location, and may in effect be tethered to the responder's movements. Although the ZCC is shown as a circular area with the responder in the center, the ZCC may be of any predetermined shape which indicates an area that is efficiently accessed by the responder. AED safe zones 180 may also be determined at this step 920.

A step of generating recommendations 922 to increase overlap of the ZCC with historical patient locations may be generated from archival location data obtained from the patient locator database 420 and the responder locator database 440. For example, if a particular patient location commonly has no overlap with a ZCC over an extended period of time, the generating recommendations step 922 may responsively issue a notification to the system administrator of the situation, and may recommend additional recruiting of responder participants who can provide the coverage. Alternative, step 922 could be disposed to automatically notify patients that they are entering a "shadow" zone of no ZCC coverage and advise them to instead conduct their current activities in a different, covered location. For example, the advice may be to shop at a mall which is an AED safe zone 180 instead of the current, uncovered, shopping mall.

Method step 930 determines a location of the patient wireless communicator relative to each of the ZCCs determined at step 920. Similarly, method step 932 determines the location of the patient wireless communicator relative to each of the AED safe zones 180. As previously described, this method step is preferably conducted automatically and by the central station 104/computer 108 based on locating data in the databases. ZCCs and safe zones overlapping with, or nearby to, the patient location are then displayed on the patient wireless communicator at ZCC displaying step 950. The displaying of the zones may be with a map display, or may be (FIG. 2) by a check box or number box indicating that the patient is within the ZCC/safe zone.

If the patient wireless communicator location does not overlap with any ZCC or safe zone, as determined by decision step 940, then a step of indicating the direction or location to the nearest such zone may be provided on the patient dashboard at step 952. Then the method loops back to the ZCC determining step at 920 to maintain dynamic updating of coverage.

If overlap is determined between one or more ZCCs and patients at decision step 940, each responder dashboard is updated with the number of patients within the respective responder wireless communicator ZCC at responder patient location displaying step 960. Optionally, location of each patient within the ZCC may be displayed at this step 960 on a dashboard map.

After each responder dashboard and patient dashboard is updated, system 100 executes a step of calculating a compensation 970 for the particular coverage time segment covered by the method. Some embodiments for calculating and accumulating such compensation are described previously with regards to FIG. 6.

Modifications to the device, method, and displays as described above are encompassed within the scope of the invention. For example, components comprising data storage hardware and/or processing software computer code may be disposed and configured into different system hardware arrangements that provide equivalent functionality of the invention. Other configurations of the system which fulfill the objectives of the described invention fall within the scope of the claims. For example, the particular appearance and arrangement of the dashboard displays may differ somewhat from the FIGUREs as long as the recited information is provided.

What is claimed is:

1. An improved cardiac emergency response system, comprising:
   a patient wireless communicator and a responder wireless communicator; and
   a central station including a computer configured with software instructions to:
      receive a wireless communication of a patient wireless communicator location from the patient wireless communicator and a wireless communication of a responder wireless communicator location from the responder wireless communicator;
      determine the patient wireless communicator location relative to a zone of cardiac coverage derived from the responder wireless communicator location in response to receiving the patient wireless communicator location and the responder wireless communicator location;
      transmit a cardiac response request to the responder wireless communicator in response to receiving a cardiac emergency response notification from the patient wireless communicator when the zone of cardiac coverage is determined by the computer to overlap the patient wireless communicator location; and
      determine a compensation to a responder to a transmission by the central station of the cardiac response request to the responder wireless communicator based the zone of cardiac coverage and the patient wireless communicator location.

2. The improved cardiac emergency response system of claim 1,
   wherein the patient wireless communicator is configured to display a representation of the patient wireless communicator location relative to the zone of cardiac coverage as determined by the central station.

3. The improved cardiac emergency response system of claim 1,
   wherein the responder wireless communicator is configured to display the patient wireless communicator location within a map of the zone of cardiac coverage when the central station determines the zone of cardiac coverage overlaps the patient wireless communicator location.

4. The improved cardiac emergency response system of claim 1, wherein the computer of the central station is configured with software instructions to further determine the compensation to the responder based an on-duty time of the responder wireless communicator.

5. The improved cardiac emergency response system of claim 1, wherein the computer of the central station is configured with software instructions to further determine the compensation to the responder based on a response time of the responder to the cardiac response request.

6. The improved cardiac emergency response system of claim 1, wherein the computer of the central station is configured with software instructions to further determine the compensation to the responder based on a cardiac rescue training status of the responder.

7. The improved cardiac emergency response system of claim 1, further comprising:
   an automated external defibrillator (AED),
      wherein the computer of the central station is configured with software instructions to further determine the compensation to the responder based on an AED location of the AED at the time of the transmission of the cardiac response request by the central station to the responder wireless communicator.

8. The improved cardiac emergency response system of claim 1,
   wherein the computer of the central station is configured with software instructions to further determine the patient wireless communicator location relative to a fixed location of a safe zone of cardiac coverage in response to receiving the patient wireless communicator location.

9. The improved cardiac emergency response system of claim 8,
   wherein the patient wireless communicator is further configured to display a representation of the patient wireless communicator location relative to the fixed location of safe zone of cardiac coverage as determined by the central station.

10. A method for administering a cardiac emergency response system including a patient wireless communicator, a responder wireless communicator and a central station, the method comprising:
    receiving, by the central station, a wireless communication of a patient wireless communicator location from the patient wireless communicator and a wireless communication of a responder wireless communicator location from the responder wireless communicator;
    determining, by the central station, the patient wireless communicator location relative to a zone of cardiac coverage derived from the responder wireless communicator location in response to receiving the patient wireless communicator location and the responder wireless communicator location;
    transmitting, by the central station, a cardiac response request to the responder wireless communicator in response to receiving a cardiac emergency response notification from the patient wireless communicator when the central station determines the zone of cardiac coverage overlaps the patient wireless communicator location; and
    determining, by the central station, a compensation to a responder to a transmission by the central station of the cardiac response request to the responder wireless communicator based on the zone of cardiac coverage and the patient wireless communicator location.

11. The method of claim 10, further comprising:
    displaying, by the patient wireless communicator, a representation of the patient wireless communicator location relative to the zone of cardiac coverage as determined by the central station.

12. The method of claim 10, further comprising:
    displaying, by the responder wireless communicator, the patient wireless communicator location within a map of the zone of cardiac coverage when the central station determines the zone of cardiac coverage overlaps the patient wireless communicator location.

13. The method of claim 10, wherein the determining, by the central station, of the compensation to the responder is further based an on-duty time of the responder wireless communicator.

14. The method of claim 10, wherein the determining, by the central station, of the compensation to the responder is further based on a response time of the responder to the cardiac response request.

15. The method of claim 10, wherein the determining, by the central station, of the compensation to the responder is further based on a cardiac rescue training status of the responder.

16. The method of claim 10, wherein the determining, by the central station, of the compensation to the responder is further based a location of an Automated External Defibrillator at the time of the transmission of the cardiac response request by the central station to the responder wireless communicator.

17. The method of claim 10, further comprising:
   determining, by the central station, the patient wireless communicator location relative to a fixed location of a safe zone of cardiac coverage in response to receiving the patient wireless communicator location from the patient wireless communicator.

18. The method of claim 17, further comprising:
   displaying, by the patient wireless communicator, a representation of the patient wireless communicator location relative to the fixed location of the safe zone of cardiac coverage as determined by the central station.

* * * * *